(12) United States Patent
Burbank et al.

(10) Patent No.: US 8,224,424 B2
(45) Date of Patent: *Jul. 17, 2012

(54) TISSUE SITE MARKERS FOR IN VIVO IMAGING

(75) Inventors: Fred H. Burbank, Laguna Niguel, CA (US); Paul Lubock, Laguna Niguel, CA (US); Michael L. Jones, Capistrano Beach, CA (US); Richard L. Quick, Mission Viejo, CA (US); Frank Louw, Carlsbad, CA (US); Stephen A. De Santis, Laguna Niguel, CA (US)

(73) Assignee: Senorx, Inc., Irvine, CA (US)

( * ) Notice: Subject to any disclaimer, the term of this patent is extended or adjusted under 35 U.S.C. 154(b) by 92 days.

This patent is subject to a terminal disclaimer.

(21) Appl. No.: 12/460,052

(22) Filed: Jul. 13, 2009

(65) Prior Publication Data

US 2010/0010342 A1    Jan. 14, 2010

Related U.S. Application Data

(63) Continuation of application No. 11/238,201, filed on Sep. 29, 2005, now Pat. No. 7,565,191, which is a continuation of application No. 10/823,053, filed on Apr. 12, 2004, now Pat. No. 6,993,375, which is a continuation of application No. 09/717,909, filed on Nov. 20, 2000, now Pat. No. 6,725,083, which is a continuation-in-part of application No. 09/241,936, filed on Feb. 2, 1999, now Pat. No. 6,161,034, and a continuation-in-part of application No. 09/343,975, filed on Jun. 30, 1999, now Pat. No. 6,347,241.

(51) Int. Cl.
*A61B 5/00* (2006.01)
*A61B 6/00* (2006.01)
*A61B 19/00* (2006.01)

(52) U.S. Cl. ........ 600/431; 600/414; 600/420; 600/426; 600/458

(58) Field of Classification Search ........................ None
See application file for complete search history.

(56) References Cited

U.S. PATENT DOCUMENTS 2,192,270 A    3/1940    McGowan
(Continued)

FOREIGN PATENT DOCUMENTS

DE    1029528 B    5/1958
(Continued)

OTHER PUBLICATIONS

Armstrong, J. S. et al. "differential marking of Excision Planes in Screened Breast lesions by Organically Coloured Gelatins", *Journal of Clincal Pathology*, Jul. 1990, No. 43(7) pp. 604-607, XP000971447 abstract; tables 1, 2.

(Continued)

*Primary Examiner* — Joseph M Pelham (57) ABSTRACT

The invention is directed biopsy site markers and methods of marking a biopsy site, so that the location of the biopsy cavity is readily visible by conventional imaging methods, particularly by ultrasonic imaging. The biopsy site markers of the invention have high ultrasound reflectivity, presenting a substantial acoustic signature from a small marker, so as to avoid obscuring diagnostic tissue features in subsequent imaging studies, and can be readily distinguished from biological features. The several disclosed embodiments of the biopsy site marker of the invention have a high contrast of acoustic impedance as placed in a tissue site, so as to efficiently reflect and scatter ultrasonic energy, and preferably include gas-filled internal pores. The markers may have a non-uniform surface contour to enhance the acoustic signature. The markers have a characteristic form which is recognizably artificial during medical imaging. The biopsy site marker may be accurately fixed to the biopsy site so as to resist migration from the biopsy cavity when a placement instrument is withdrawn, and when the marked tissue is subsequently moved or manipulated.

13 Claims, 8 Drawing Sheets

U.S. PATENT DOCUMENTS

| | | |
|---|---|---|
| 2,481,408 A | 9/1949 | Fuller et al. |
| 2,832,888 A | 4/1958 | Houston |
| 2,899,362 A | 8/1959 | Sieger, Jr. et al. |
| 2,907,327 A | 10/1959 | White |
| 3,341,417 A | 9/1967 | Sinaiko |
| 3,402,712 A | 9/1968 | Eisenhand |
| 3,516,412 A | 6/1970 | Ackerman |
| 3,593,343 A | 7/1971 | Viggers |
| 3,757,781 A | 9/1973 | Smart |
| 3,818,894 A | 6/1974 | Wichterle et al. |
| 3,823,212 A | 7/1974 | Chvapil |
| 3,921,632 A | 11/1975 | Bardani |
| 4,005,699 A | 2/1977 | Bucalo |
| 4,007,732 A | 2/1977 | Kvavle et al. |
| 4,041,931 A | 8/1977 | Elliott et al. |
| 4,103,690 A | 8/1978 | Harris |
| 4,105,030 A | 8/1978 | Kercso |
| 4,172,449 A | 10/1979 | LeRoy et al. |
| 4,197,846 A | 4/1980 | Bucalo |
| 4,217,889 A | 8/1980 | Radovan et al. |
| 4,276,885 A | 7/1981 | Tickner et al. |
| 4,294,241 A | 10/1981 | Miyata |
| 4,298,998 A | 11/1981 | Naficy |
| 4,331,654 A | 5/1982 | Morris |
| 4,390,018 A | 6/1983 | Zukowski |
| 4,400,170 A | 8/1983 | McNaughton et al. |
| 4,401,124 A | 8/1983 | Guess et al. |
| 4,405,314 A | 9/1983 | Cope |
| 4,428,082 A | 1/1984 | Naficy |
| 4,438,253 A | 3/1984 | Casey et al. |
| 4,442,843 A | 4/1984 | Rasor et al. |
| 4,470,160 A | 9/1984 | Cavon |
| 4,487,209 A | 12/1984 | Mehl |
| 4,545,367 A | 10/1985 | Tucci |
| 4,549,560 A | 10/1985 | Andis |
| 4,582,061 A | 4/1986 | Fry |
| 4,582,640 A | 4/1986 | Smestad et al. |
| 4,588,395 A | 5/1986 | Lemelson |
| 4,597,753 A | 7/1986 | Turley |
| 4,647,480 A | 3/1987 | Ahmed |
| 4,655,226 A | 4/1987 | Lee |
| 4,661,103 A | 4/1987 | Harman |
| 4,682,606 A | 7/1987 | DeCaprio |
| 4,693,237 A | 9/1987 | Hoffman et al. |
| 4,740,208 A | 4/1988 | Cavon |
| 4,813,062 A | 3/1989 | Gilpatrick |
| 4,820,267 A | 4/1989 | Harman |
| 4,832,680 A | 5/1989 | Haber et al. |
| 4,832,686 A | 5/1989 | Anderson |
| 4,847,049 A | 7/1989 | Yamamoto |
| 4,863,470 A | 9/1989 | Cater |
| 4,870,966 A | 10/1989 | Dellon et al. |
| 4,874,376 A | 10/1989 | Hawkins, Jr. |
| 4,889,707 A | 12/1989 | Day et al. |
| 4,909,250 A | 3/1990 | Smith |
| 4,938,763 A | 7/1990 | Dunn et al. |
| 4,950,665 A | 8/1990 | Floyd |
| 4,963,150 A | 10/1990 | Brauman |
| 4,970,298 A | 11/1990 | Silver et al. |
| 4,989,608 A | 2/1991 | Ratner |
| 4,994,028 A | 2/1991 | Leonard et al. |
| 5,012,818 A | 5/1991 | Joishy |
| 5,059,197 A | 10/1991 | Urie et al. |
| 5,081,997 A | 1/1992 | Bosley et al. |
| 5,120,802 A | 6/1992 | Mares et al. |
| 5,125,413 A | 6/1992 | Baran |
| 5,137,928 A | 8/1992 | Erbel et al. |
| 5,141,748 A | 8/1992 | Rizzo |
| 5,147,307 A | 9/1992 | Gluck |
| 5,147,631 A | 9/1992 | Glajch et al. |
| 5,162,430 A | 11/1992 | Rhee et al. |
| 5,163,896 A | 11/1992 | Suthanthiran et al. |
| 5,195,540 A | 3/1993 | Shiber |
| 5,199,441 A | 4/1993 | Hogle |
| 5,219,339 A | 6/1993 | Saito |
| 5,221,269 A | 6/1993 | Miller et al. |
| 5,231,615 A | 7/1993 | Endoh |
| 5,236,410 A | 8/1993 | Granov et al. |
| 5,242,759 A | 9/1993 | Hall |
| 5,250,026 A | 10/1993 | Ehrlich et al. |
| 5,271,961 A | 12/1993 | Mathiowitz et al. |
| 5,273,532 A | 12/1993 | Niezink et al. |
| 5,280,788 A | 1/1994 | Janes et al. |
| 5,281,197 A | 1/1994 | Arias et al. |
| 5,281,408 A | 1/1994 | Unger |
| 5,282,781 A | 2/1994 | Liprie |
| 5,284,479 A | 2/1994 | de Jong |
| 5,289,831 A | 3/1994 | Bosley |
| 5,320,613 A | 6/1994 | Houge et al. |
| 5,328,955 A | 7/1994 | Rhee et al. |
| 5,334,381 A | 8/1994 | Unger |
| 5,353,804 A | 10/1994 | Kornberg et al. |
| 5,354,623 A | 10/1994 | Hall |
| 5,366,756 A | 11/1994 | Chesterfield et al. |
| 5,368,030 A | 11/1994 | Zinreich et al. |
| 5,388,588 A | 2/1995 | Nabai et al. |
| 5,394,875 A | 3/1995 | Lewis et al. |
| 5,395,319 A | 3/1995 | Hirsch et al. |
| 5,409,004 A | 4/1995 | Sloan |
| 5,417,708 A | 5/1995 | Hall et al. |
| 5,422,730 A | 6/1995 | Barlow et al. |
| 5,425,366 A | 6/1995 | Reinhardt et al. |
| 5,433,204 A | 7/1995 | Olson |
| 5,449,560 A | 9/1995 | Antheunis et al. |
| 5,451,406 A | 9/1995 | Lawin et al. |
| 5,460,182 A | 10/1995 | Goodman et al. |
| 5,469,847 A | 11/1995 | Zinreich et al. |
| 5,475,052 A | 12/1995 | Rhee et al. |
| 5,490,521 A | 2/1996 | Davis et al. |
| 5,494,030 A | 2/1996 | Swartz et al. |
| 5,499,989 A | 3/1996 | LaBash |
| 5,507,807 A | 4/1996 | Shippert |
| 5,508,021 A | 4/1996 | Grinstaff et al. |
| 5,514,085 A | 5/1996 | Yoon |
| 5,522,896 A | 6/1996 | Prescott |
| 5,538,726 A | 7/1996 | Order |
| 5,542,915 A | 8/1996 | Edwards et al. |
| 5,549,560 A | 8/1996 | Van de Wijdeven |
| RE35,391 E | 12/1996 | Brauman |
| 5,580,568 A | 12/1996 | Greff et al. |
| 5,585,112 A | 12/1996 | Unger et al. |
| 5,611,352 A | 3/1997 | Kobren et al. |
| 5,626,611 A | 5/1997 | Liu et al. |
| 5,628,781 A | 5/1997 | Williams et al. |
| 5,629,008 A | 5/1997 | Lee |
| 5,636,255 A | 6/1997 | Ellis |
| 5,643,246 A | 7/1997 | Leeb et al. |
| 5,646,146 A | 7/1997 | Faarup et al. |
| 5,667,767 A | 9/1997 | Greff et al. |
| 5,673,841 A | 10/1997 | Schulze et al. |
| 5,676,146 A | 10/1997 | Scarborough |
| 5,676,925 A | 10/1997 | Klaveness et al. |
| 5,688,490 A | 11/1997 | Tournier et al. |
| 5,690,120 A | 11/1997 | Jacobsen et al. |
| 5,695,480 A | 12/1997 | Evans et al. |
| 5,702,128 A | 12/1997 | Maxim et al. |
| 5,702,716 A | 12/1997 | Dunn et al. |
| 5,747,060 A | 5/1998 | Sackler et al. |
| 5,762,903 A | 6/1998 | Park et al. |
| 5,769,086 A | 6/1998 | Ritchart et al. |
| 5,776,496 A | 7/1998 | Violante et al. |
| 5,779,647 A | 7/1998 | Chau et al. |
| 5,782,764 A | 7/1998 | Werne |
| 5,782,775 A | 7/1998 | Milliman et al. |
| 5,795,308 A | 8/1998 | Russin |
| 5,800,362 A | 9/1998 | Kobren et al. |
| 5,800,389 A | 9/1998 | Burney et al. |
| 5,800,445 A | 9/1998 | Ratcliff et al. |
| 5,800,541 A | 9/1998 | Rhee et al. |
| 5,817,022 A | 10/1998 | Vesely |
| 5,820,918 A | 10/1998 | Ronan et al. |
| 5,821,184 A | 10/1998 | Haines et al. |
| 5,823,198 A | 10/1998 | Jones et al. |
| 5,824,042 A | 10/1998 | Lombardi et al. |
| 5,824,081 A | 10/1998 | Knapp et al. |
| 5,830,178 A | 11/1998 | Jones et al. |
| 5,842,477 A | 12/1998 | Naughton et al. |

| | | | |
|---|---|---|---|
| 5,842,999 A | 12/1998 | Pruitt et al. |
| 5,845,646 A | 12/1998 | Lemelson |
| 5,846,220 A | 12/1998 | Elsberry |
| 5,851,508 A | 12/1998 | Greff et al. |
| 5,853,366 A | 12/1998 | Dowlatshahi |
| 5,865,806 A | 2/1999 | Howell |
| 5,869,080 A | 2/1999 | McGregor et al. |
| 5,876,340 A | 3/1999 | Tu et al. |
| 5,879,357 A | 3/1999 | Heaton et al. |
| 5,891,558 A | 4/1999 | Bell et al. |
| 5,897,507 A | 4/1999 | Kortenbach et al. |
| 5,902,310 A | 5/1999 | Foerster et al. |
| 5,911,705 A | 6/1999 | Howell |
| 5,921,933 A | 7/1999 | Sarkis et al. |
| 5,922,024 A | 7/1999 | Janzen et al. |
| 5,928,626 A | 7/1999 | Klaveness et al. |
| 5,928,773 A | 7/1999 | Andersen |
| 5,941,890 A | 8/1999 | Voegele et al. |
| 5,942,209 A | 8/1999 | Leavitt et al. |
| 5,948,425 A | 9/1999 | Janzen et al. |
| 5,954,670 A | 9/1999 | Baker |
| 5,972,817 A | 10/1999 | Haines et al. |
| 5,989,265 A | 11/1999 | Bouquet De La Joliniere et al. |
| 6,015,541 A | 1/2000 | Greff et al. |
| 6,030,333 A | 2/2000 | Sioshansi et al. |
| 6,053,925 A | 4/2000 | Barnhart |
| 6,056,700 A | 5/2000 | Burney et al. |
| 6,066,122 A | 5/2000 | Fisher |
| 6,066,325 A | 5/2000 | Wallace et al. |
| 6,071,301 A | 6/2000 | Cragg et al. |
| 6,071,310 A | 6/2000 | Picha et al. |
| 6,071,496 A | 6/2000 | Stein et al. |
| 6,096,065 A | 8/2000 | Crowley |
| 6,096,070 A | 8/2000 | Ragheb et al. |
| 6,106,473 A | 8/2000 | Violante et al. |
| 6,117,108 A | 9/2000 | Woehr et al. |
| 6,120,536 A | 9/2000 | Ding et al. |
| 6,142,955 A | 11/2000 | Farascioni et al. |
| 6,159,445 A | 12/2000 | Klaveness et al. |
| 6,161,034 A | 12/2000 | Burbank et al. |
| 6,162,192 A | 12/2000 | Cragg et al. |
| 6,174,330 B1 | 1/2001 | Stinson |
| 6,177,062 B1 | 1/2001 | Stein et al. |
| 6,181,960 B1 | 1/2001 | Jensen et al. |
| 6,183,497 B1 | 2/2001 | Sing et al. |
| 6,190,350 B1 | 2/2001 | Davis et al. |
| 6,200,258 B1 | 3/2001 | Slater et al. |
| 6,203,524 B1 | 3/2001 | Burney et al. |
| 6,203,568 B1 | 3/2001 | Lombardi et al. |
| 6,213,957 B1 | 4/2001 | Milliman et al. |
| 6,214,045 B1 | 4/2001 | Corbitt, Jr. et al. |
| 6,214,315 B1 | 4/2001 | Greff et al. |
| 6,220,248 B1 | 4/2001 | Voegele et al. |
| 6,224,630 B1 | 5/2001 | Bao et al. |
| 6,228,049 B1 | 5/2001 | Schroeder et al. |
| 6,228,055 B1 | 5/2001 | Foerster et al. |
| 6,231,615 B1 | 5/2001 | Preissman |
| 6,234,177 B1 | 5/2001 | Barsch |
| 6,241,687 B1 | 6/2001 | Voegele et al. |
| 6,241,734 B1 | 6/2001 | Scribner et al. |
| 6,251,418 B1 | 6/2001 | Ahern et al. |
| 6,261,243 B1 | 7/2001 | Burney et al. |
| 6,261,302 B1 | 7/2001 | Voegele et al. |
| 6,264,917 B1 | 7/2001 | Klaveness et al. |
| 6,270,464 B1 | 8/2001 | Fulton, III et al. |
| 6,287,278 B1 | 9/2001 | Woehr et al. |
| 6,287,332 B1 | 9/2001 | Bolz et al. |
| 6,289,229 B1 | 9/2001 | Crowley |
| 6,312,429 B1 | 11/2001 | Burbank et al. |
| 6,316,522 B1 | 11/2001 | Loomis et al. |
| 6,335,029 B1 | 1/2002 | Kamath et al. |
| 6,336,904 B1 | 1/2002 | Nikolchev |
| 6,340,367 B1 | 1/2002 | Stinson et al. |
| 6,343,227 B1 | 1/2002 | Crowley |
| 6,347,240 B1 | 2/2002 | Foley et al. |
| 6,347,241 B2 | 2/2002 | Burbank et al. |
| 6,350,244 B1 | 2/2002 | Fisher |
| 6,350,274 B1 | 2/2002 | Li |
| 6,354,989 B1 | 3/2002 | Nudeshima |
| 6,356,112 B1 | 3/2002 | Tran et al. |
| 6,356,782 B1 | 3/2002 | Sirimanne et al. |
| 6,358,217 B1 | 3/2002 | Bourassa |
| 6,363,940 B1 | 4/2002 | Krag |
| 6,371,904 B1 | 4/2002 | Sirimanne et al. |
| 6,394,965 B1 | 5/2002 | Klein |
| 6,403,758 B1 | 6/2002 | Loomis |
| 6,405,733 B1 | 6/2002 | Fogarty et al. |
| 6,409,742 B1 | 6/2002 | Fulton, III et al. |
| 6,424,857 B1 | 7/2002 | Henrichs et al. |
| 6,425,903 B1 | 7/2002 | Voegele |
| 6,450,937 B1 | 9/2002 | Mercereau et al. |
| 6,450,938 B1 | 9/2002 | Miller |
| 6,471,700 B1 | 10/2002 | Burbank et al. |
| 6,478,790 B2 | 11/2002 | Bardani |
| 6,506,156 B1 | 1/2003 | Jones et al. |
| 6,511,468 B1 | 1/2003 | Cragg et al. |
| 6,537,193 B1 | 3/2003 | Lennox |
| 6,540,981 B2 | 4/2003 | Klaveness et al. |
| 6,544,185 B2 | 4/2003 | Montegrande |
| 6,551,253 B2 | 4/2003 | Worm et al. |
| 6,554,760 B2 | 4/2003 | Lamoureux et al. |
| 6,562,317 B2 | 5/2003 | Greff et al. |
| 6,564,806 B1 | 5/2003 | Fogarty et al. |
| 6,565,551 B1 | 5/2003 | Jones et al. |
| 6,567,689 B2 | 5/2003 | Burbank et al. |
| 6,575,888 B2 | 6/2003 | Zamora et al. |
| 6,575,991 B1 | 6/2003 | Chesbrough et al. |
| 6,605,047 B2 | 8/2003 | Zarins et al. |
| 6,610,026 B2 | 8/2003 | Cragg et al. |
| 6,613,002 B1 | 9/2003 | Clark et al. |
| 6,616,630 B1 | 9/2003 | Woehr et al. |
| 6,626,850 B1 | 9/2003 | Chau et al. |
| 6,628,982 B1 | 9/2003 | Thomas et al. |
| 6,636,758 B2 | 10/2003 | Sanchez et al. |
| 6,638,234 B2 | 10/2003 | Burbank et al. |
| 6,638,308 B2 | 10/2003 | Corbitt, Jr. et al. |
| 6,652,442 B2 | 11/2003 | Gatto |
| 6,656,192 B2 | 12/2003 | Esposito et al. |
| 6,699,205 B2 | 3/2004 | Fulton et al. |
| 6,712,774 B2 | 3/2004 | Voegele et al. |
| 6,712,836 B1 | 3/2004 | Berg et al. |
| 6,716,444 B1 | 4/2004 | Castro et al. |
| 6,725,083 B1 | 4/2004 | Burbank et al. |
| 6,730,042 B2 | 5/2004 | Fulton et al. |
| 6,730,044 B2 | 5/2004 | Stephens et al. |
| 6,746,661 B2 | 6/2004 | Kaplan |
| 6,746,773 B2 | 6/2004 | Llanos et al. |
| 6,752,154 B2 | 6/2004 | Fogarty et al. |
| 6,766,186 B1 | 7/2004 | Hoyns et al. |
| 6,774,278 B1 | 8/2004 | Ragheb et al. |
| 6,780,179 B2 | 8/2004 | Lee et al. |
| 6,824,507 B2 | 11/2004 | Miller |
| 6,824,527 B2 | 11/2004 | Gollobin |
| 6,846,320 B2 | 1/2005 | Ashby et al. |
| 6,862,470 B2 | 3/2005 | Burbank et al. |
| 6,863,685 B2 | 3/2005 | Davila et al. |
| 6,899,731 B2 | 5/2005 | Li et al. |
| 6,918,927 B2 | 7/2005 | Bates et al. |
| 6,936,014 B2 | 8/2005 | Vetter et al. |
| 6,939,318 B2 | 9/2005 | Stenzel |
| 6,945,973 B2 | 9/2005 | Bray |
| 6,951,564 B2 | 10/2005 | Espositio et al. |
| 6,994,712 B1 | 2/2006 | Fisher et al. |
| 7,001,341 B2 | 2/2006 | Gellman et al. |
| 7,008,382 B2 | 3/2006 | Adams et al. |
| 7,014,610 B2 | 3/2006 | Koulik |
| 7,025,765 B2 | 4/2006 | Balbierz et al. |
| 7,044,957 B2 | 5/2006 | Foerster et al. |
| 7,083,576 B2 | 8/2006 | Zarins et al. |
| 7,125,397 B2 | 10/2006 | Woehr et al. |
| 7,172,549 B2 | 2/2007 | Slater et al. |
| 7,214,211 B2 | 5/2007 | Woehr et al. |
| 7,229,417 B2 | 6/2007 | Foerster et al. |
| 7,236,816 B2 | 6/2007 | Kumar et al. |
| 7,264,613 B2 | 9/2007 | Woehr et al. |
| 7,294,118 B2 | 11/2007 | Saulenas et al. |
| 7,297,725 B2 | 11/2007 | Winterton et al. |
| 7,329,402 B2 | 2/2008 | Unger et al. |

| | | |
|---|---|---|
| 7,416,533 B2 | 8/2008 | Gellman et al. |
| 7,449,000 B2 | 11/2008 | Adams et al. |
| 7,527,610 B2 | 5/2009 | Erickson |
| 7,534,452 B2 | 5/2009 | Chernomorsky et al. |
| 7,569,065 B2 | 8/2009 | Chesbrough et al. |
| 7,637,948 B2 | 12/2009 | Corbitt, Jr. |
| 7,651,505 B2 | 1/2010 | Lubock et al. |
| 2001/0003791 A1 | 6/2001 | Burbank et al. |
| 2001/0006616 A1 | 7/2001 | Leavitt et al. |
| 2001/0049481 A1 | 12/2001 | Fulton, III et al. |
| 2002/0004060 A1 | 1/2002 | Heublein et al. |
| 2002/0016625 A1 | 2/2002 | Falotico et al. |
| 2002/0022883 A1 | 2/2002 | Burg |
| 2002/0026201 A1 | 2/2002 | Foerster et al. |
| 2002/0035324 A1 | 3/2002 | Sirimanne et al. |
| 2002/0038087 A1 | 3/2002 | Burbank et al. |
| 2002/0045842 A1 | 4/2002 | Van Bladel et al. |
| 2002/0052572 A1 | 5/2002 | Franco et al. |
| 2002/0055731 A1 | 5/2002 | Atala et al. |
| 2002/0058868 A1 | 5/2002 | Hoshino et al. |
| 2002/0058882 A1 | 5/2002 | Fulton, III et al. |
| 2002/0077687 A1 | 6/2002 | Ahn |
| 2002/0082519 A1 | 6/2002 | Miller et al. |
| 2002/0082682 A1 | 6/2002 | Barclay et al. |
| 2002/0082683 A1 | 6/2002 | Stinson et al. |
| 2002/0095204 A1 | 7/2002 | Thompson et al. |
| 2002/0095205 A1 | 7/2002 | Edwin et al. |
| 2002/0107437 A1 | 8/2002 | Sirimanne et al. |
| 2002/0133148 A1 | 9/2002 | Daniel et al. |
| 2002/0143359 A1 | 10/2002 | Fulton, III et al. |
| 2002/0165608 A1 | 11/2002 | Llanos et al. |
| 2002/0188196 A1 | 12/2002 | Burbank et al. |
| 2002/0193815 A1 | 12/2002 | Foerster et al. |
| 2002/0193867 A1 | 12/2002 | Gladdish, Jr. et al. |
| 2003/0036803 A1 | 2/2003 | McGhan |
| 2003/0051735 A1 | 3/2003 | Pavcnik et al. |
| 2003/0116806 A1 | 6/2003 | Kato |
| 2003/0165478 A1 | 9/2003 | Sokoll |
| 2003/0191355 A1 | 10/2003 | Ferguson |
| 2003/0199887 A1 | 10/2003 | Ferrera et al. |
| 2003/0225420 A1 | 12/2003 | Wardle |
| 2003/0233101 A1 | 12/2003 | Lubock et al. |
| 2003/0236573 A1 | 12/2003 | Evans et al. |
| 2004/0002650 A1 | 1/2004 | Mandrusov et al. |
| 2004/0016195 A1 | 1/2004 | Archuleta |
| 2004/0024304 A1 | 2/2004 | Foerster et al. |
| 2004/0059341 A1 | 3/2004 | Gellman et al. |
| 2004/0073107 A1 | 4/2004 | Sioshansi et al. |
| 2004/0073284 A1 | 4/2004 | Bates et al. |
| 2004/0097981 A1 | 5/2004 | Selis |
| 2004/0101479 A1 | 5/2004 | Burbank et al. |
| 2004/0106891 A1 | 6/2004 | Langan et al. |
| 2004/0116802 A1 | 6/2004 | Jessop et al. |
| 2004/0116806 A1 | 6/2004 | Burbank et al. |
| 2004/0124105 A1 | 7/2004 | Seiler et al. |
| 2004/0127765 A1 | 7/2004 | Seiler et al. |
| 2004/0162574 A1 | 8/2004 | Viola |
| 2004/0167619 A1 | 8/2004 | Case et al. |
| 2004/0193044 A1 | 9/2004 | Burbank et al. |
| 2004/0204660 A1 | 10/2004 | Fulton et al. |
| 2004/0210208 A1 | 10/2004 | Paul et al. |
| 2004/0213756 A1 | 10/2004 | Michal et al. |
| 2004/0236211 A1 | 11/2004 | Burbank et al. |
| 2004/0236212 A1 | 11/2004 | Lubock et al. |
| 2004/0236213 A1 | 11/2004 | Jones et al. |
| 2005/0020916 A1 | 1/2005 | MacFarlane et al. |
| 2005/0033157 A1 | 2/2005 | Klien et al. |
| 2005/0033195 A1 | 2/2005 | Fulton et al. |
| 2005/0036946 A1 | 2/2005 | Pathak et al. |
| 2005/0045192 A1 | 3/2005 | Fulton et al. |
| 2005/0059887 A1 | 3/2005 | Mostafavi et al. |
| 2005/0059888 A1 | 3/2005 | Sirimanne et al. |
| 2005/0063908 A1 | 3/2005 | Burbank et al. |
| 2005/0065354 A1 | 3/2005 | Roberts |
| 2005/0065453 A1 | 3/2005 | Shabaz et al. |
| 2005/0080337 A1 | 4/2005 | Sirimanne et al. |
| 2005/0080339 A1 | 4/2005 | Sirimanne et al. |
| 2005/0085724 A1 | 4/2005 | Sirimanne et al. |
| 2005/0100580 A1 | 5/2005 | Osborne et al. |
| 2005/0113659 A1 | 5/2005 | Pothier et al. |
| 2005/0119562 A1 | 6/2005 | Jones et al. |
| 2005/0143650 A1 | 6/2005 | Winkel |
| 2005/0143656 A1 | 6/2005 | Burbank et al. |
| 2005/0165305 A1 | 7/2005 | Foerster et al. |
| 2005/0175657 A1 | 8/2005 | Hunter et al. |
| 2005/0181007 A1 | 8/2005 | Hunter et al. |
| 2005/0234336 A1 | 10/2005 | Beckman et al. |
| 2005/0268922 A1 | 12/2005 | Conrad et al. |
| 2005/0273002 A1 | 12/2005 | Goosen et al. |
| 2005/0277871 A1 | 12/2005 | Selis |
| 2006/0004440 A1 | 1/2006 | Stinson |
| 2006/0009800 A1 | 1/2006 | Christianson et al. |
| 2006/0036158 A1 | 2/2006 | Field et al. |
| 2006/0036159 A1 | 2/2006 | Sirimanne et al. |
| 2006/0074443 A1 | 4/2006 | Foerster et al. |
| 2006/0079770 A1 | 4/2006 | Sirimanne et al. |
| 2006/0079805 A1 | 4/2006 | Miller et al. |
| 2006/0079829 A1 | 4/2006 | Fulton et al. |
| 2006/0079888 A1 | 4/2006 | Mulier et al. |
| 2006/0122503 A1 | 6/2006 | Burbank et al. |
| 2006/0155190 A1 | 7/2006 | Burbank et al. |
| 2006/0173296 A1 | 8/2006 | Miller et al. |
| 2006/0177379 A1 | 8/2006 | Asgari |
| 2006/0217635 A1 | 9/2006 | McCombs et al. |
| 2006/0235298 A1 | 10/2006 | Kotmel et al. |
| 2006/0241385 A1 | 10/2006 | Dietz |
| 2007/0021642 A1 | 1/2007 | Lamoureux et al. |
| 2007/0083132 A1 | 4/2007 | Sharrow |
| 2007/0135711 A1 | 6/2007 | Chernomorsky et al. |
| 2007/0142725 A1 | 6/2007 | Hardin et al. |
| 2007/0167736 A1 | 7/2007 | Dietz et al. |
| 2007/0167749 A1 | 7/2007 | Yarnall et al. |
| 2007/0239118 A1 | 10/2007 | Ono et al. |
| 2007/0287933 A1 | 12/2007 | Phan et al. |
| 2008/0097199 A1 | 4/2008 | Mullen |
| 2008/0188768 A1 | 8/2008 | Zarins et al. |
| 2008/0269638 A1 | 10/2008 | Cooke et al. |
| 2009/0000629 A1 | 1/2009 | Hornscheidt et al. |
| 2009/0024225 A1 | 1/2009 | Stubbs |
| 2009/0069713 A1 | 3/2009 | Adams et al. |
| 2009/0076484 A1 | 3/2009 | Fukaya |
| 2009/0131825 A1 | 5/2009 | Burbank et al. |

FOREIGN PATENT DOCUMENTS

| | | |
|---|---|---|
| EP | 0 146 699 | 9/1984 |
| EP | 0 255 123 | 7/1987 |
| EP | 0 292 936 | 5/1988 |
| EP | 0 386 936 | 9/1990 |
| EP | 0 481 685 | 10/1991 |
| EP | 0 458 745 | 11/1991 |
| EP | 0475077 A2 | 3/1992 |
| EP | 0 552 924 | 1/1993 |
| EP | 0769281 A2 | 4/1997 |
| EP | 1114618 A2 | 7/2001 |
| EP | 1163888 A1 | 12/2001 |
| EP | 1281416 A2 | 6/2002 |
| EP | 1364628 A1 | 11/2003 |
| EP | 1493451 A1 | 1/2005 |
| EP | 1767167 A2 | 3/2007 |
| FR | 2646674 A3 | 11/1990 |
| GB | 708148 | 4/1954 |
| JP | 2131757 A | 5/1990 |
| WO | WO 89/06978 | 8/1989 |
| WO | WO 91/12823 | 9/1991 |
| WO | WO 93/14712 | 5/1993 |
| WO | 9317671 A1 | 9/1993 |
| WO | WO 93/17718 | 9/1993 |
| WO | 9416647 A1 | 8/1994 |
| WO | 9507057 A1 | 3/1995 |
| WO | WO 96/08208 | 3/1996 |
| WO | WO 98/06346 | 2/1998 |
| WO | 9908607 A1 | 2/1999 |
| WO | WO 99/30764 | 6/1999 |
| WO | 9935966 A1 | 7/1999 |
| WO | 9951143 A1 | 10/1999 |
| WO | 0023124 A1 | 4/2000 |

| | | | |
|---|---|---|---|
| WO | 0028554 A1 | 5/2000 |
| WO | WO 00/24332 | 5/2000 |
| WO | 0038779 A1 | 7/2000 |
| WO | WO 00/38579 | 7/2000 |
| WO | 0054689 A1 | 9/2000 |
| WO | 0100101 A1 | 1/2001 |
| WO | WO 01/08578 | 2/2001 |
| WO | 0170114 A1 | 9/2001 |
| WO | 0207786 A2 | 1/2002 |
| WO | 0241786 A2 | 5/2002 |
| WO | 03000308 A1 | 1/2003 |
| WO | 2004045444 A2 | 6/2004 |
| WO | 2005013832 A1 | 2/2005 |
| WO | 2005089664 A1 | 9/2005 |
| WO | 2006056739 A2 | 6/2006 |
| WO | 2006097331 A2 | 9/2006 |
| WO | 2006105353 A2 | 10/2006 |
| WO | 2007069105 A2 | 6/2007 |
| WO | 2008077081 A2 | 6/2008 |

OTHER PUBLICATIONS

Fucci, V., et al, "Large Bowel Transit Times Using Radiopaque Markers in Normal Cats", *J. of Am. Animal Hospital Assn.*, Nov.-Dec. 31, 1995 (6) 473-7.

Schindlbeck, N. E., et al., "Measurement of Colon Transit Time", *J. of Gastroenterology*, No. 28, pp. 399-404, 1990.

Shiga et al, Preparation of Poly(D, L-lactide) and Copoly(lactide-glycolide) Microspheres of Uniform Size, *J. Pharm. Pharmacol.* 1996 48:891-895.

Eiselt, P. et al, "Development of Technologies Aiding Large—Tissue Engineering", Biotechnol. Prog., vol. 14, No. 1, pp. 134-140, 1998.

Press release for Biopsys Ethicon Endo-Surgery (Europe) GmbH; The Mammotome Vacuum Biopsy System. From: http://www.medicine-news.com/articles/devices/mammotome.html. 3 pages, 1998.

Johnson & Johnson: Breast Biopsy (minimally invasive): Surgical Technique: Steps in the Mamotome Surgical Procedure. From http://www.jnjgateway.com. 3 pages, 2000.

Johnson & Johnson: New Minimally Invasive Breast Biopsy Device Receives Marketing Clearance in Canada; Aug. 6, 1999. From http://www.jnjgateway.com. 4 pages.

Johnson & Johnson: Mammotome Hand Held Receives FDA Marketing Clearance for Minimally Invasive Breast Biopises; Sep. 1, 1999. From From http://www.jnjgateway.com. 5 pages.

Johnson & Johnson: The Mammotome Breast Biopsy System. From: http://www.breastcareinfo.com/aboutm.htm. 6 pages, 1998.

Cook Incorporated: Emoblization and Occlusion. From: www.cookgroup.com 6 pages, 1998.

Liberman, Laura, et al. Percutaneous Removal of Malignant Mammographic Lesions at Stereotactic Vacuum-assisted Biopsy. From: The Departments of Radiology, Pathology, and Surgery. Memorial Sloan-Kettering Cancer Center. From the 1997 RSNA scientific assembly. vol. 206, No. 3. pp. 711-715.

TISSUE SITE MARKERS FOR IN VIVO IMAGING

RELATED APPLICATIONS

This application is a continuation application prior application Ser. No. 11/238,201, filed Sep. 29, 2005, now U.S. Pat. No. 7,565,191, which is a continuation of application Ser. No. 10/823,053, filed Apr. 12, 2004, now U.S. Pat. No. 6,993,375, which is continuation of Ser. No. 09/717,909, filed Nov. 20, 2000, now U.S. Pat. No. 6,725,083, which is a continuation-in-part of application Ser. No. 09/241,936, filed Feb. 2, 1999, now U.S. Pat. No. 6,161,034 and a continuation-in-part of application Ser. No. 09/343,975, filed Jun. 30, 1999, now U.S. Pat. No. 6,347,241 which are incorporated herein in their entireties by reference and from which priorities are claimed.

BACKGROUND OF THE INVENTION

In diagnosing and treating certain medical conditions, it is often desirable to perform a biopsy, in which a specimen or sample of the suspicious tissue is removed for pathological examination, tests and analysis. As is known, obtaining a tissue sample by biopsy and the subsequent examination are typically employed in the diagnosis of cancers and other malignant tumors, or to confirm that a suspected lesion or tumor is not malignant. The information obtained from these diagnostic tests and/or examinations is frequently used to devise a therapeutic plan for the appropriate surgical procedure or other course of treatment.

In many instances, the suspicious tissue to be sampled is located in a subcutaneous site, such as inside a human breast. Such removal of tissue samples may be accomplished by open surgical technique, or through the use of a specialized biopsy instrument and techniques. To minimize surgical intrusion into patient's body, it is often desirable to insert a small instrument, such as a biopsy needle, into the body for extracting the biopsy specimen while imaging the procedure using fluoroscopy, ultrasonic imaging, x-rays, MRI or any other suitable form of imaging technique. Examination of tissue samples taken by biopsy is of particular significance in the diagnosis and treatment of breast cancer. In the ensuing discussion, the biopsy and treatment site described will generally be the human breast, although the invention is suitable for marking biopsy sites in other parts of the human and other mammalian body as well.

Periodic physical examination of the breasts and mammography are important for early detection of potentially cancerous lesions. In mammography, the breast is compressed between two plates while specialized x-ray images are taken. If an abnormal mass in the breast is found by physical examination or mammography, ultrasound may be used to determine whether the mass is a solid tumor or a fluid-filled cyst. Solid masses are usually subjected to some type of tissue biopsy to determine if the mass is cancerous.

If a solid mass or lesion is large enough to be palpable, a tissue specimen can be removed from the mass by a variety of techniques, including but not limited to open surgical biopsy, a technique known as Fine Needle Aspiration Biopsy (FNAB) and instruments characterized as "vacuum assisted large core biopsy devices".

If a solid mass of the breast is small and non palpable (e.g., the type typically discovered through mammography), a relatively new biopsy procedure known as stereotactic needle biopsy may be used. In performing a stereotactic needle biopsy of a breast, the patient lies on a special biopsy table with her breast compressed between the plates of a mammography apparatus and two separate x-rays or digital video views are taken from two different points of view. A computer calculates the exact position of the lesion as well as depth of the lesion within the breast. Thereafter, a mechanical stereotactic apparatus is programmed with the coordinates and depth information calculated by the computer, and such apparatus is used to precisely advance the biopsy needle into the small lesion. Depending on the type of biopsy needle(s) used, this stereotactic technique may be used to obtain cytologic specimens, e.g., obtained through FNAB or it may be used to obtain histologic specimens e.g., obtained through coring needle biopsy. Usually at least five separate biopsy specimens are obtained from locations around the small lesion as well as one from the center of the lesion.

The available treatment options for cancerous lesions of the breast include various degrees of mastectomy or lumpectomy and radiation therapy, as well as chemotherapy and combinations of these treatments. However, radiographically visible tissue features, originally observed in a mammogram, may be removed, altered or obscured by the biopsy procedure. In order for the surgeon or radiation oncologist to direct surgical or radiation treatment to the precise location of the breast lesion several days or weeks after the biopsy procedure was performed, it is desirable that a biopsy site marker be placed in or on the patient's body to serve as a landmark for subsequent location of the lesion site. While current radiographic type markers may persist at the biopsy site, an additional mammography generally must be performed at the time of follow up treatment or surgery in order to locate the site of the previous surgery or biopsy. In addition, once the site of the previous procedure is located using mammography, the site must usually be marked with a location wire which has a barb on the end which is advanced into site of the previous procedure. The barb is meant to fix the tip of the location wire with respect to the site of the previous procedure so that the patient can then be removed from the confinement of the mammography apparatus and the follow-up procedure performed. However, as the patient is removed from the mammography apparatus, or otherwise transported the position of the location wire can change or shift in relation to the site of the previous procedure. This, in turn, can result in follow-up treatments being misdirected to an undesired portion of the patient's tissue.

As an alternative or adjunct to radiographic imaging, ultrasonic imaging and visualization techniques (herein abbreviated as "USI") can be used to image the tissue of interest at the site of interest during a surgical or biopsy procedure or follow-up procedure. USI is capable of providing precise location and imaging of suspicious tissue, surrounding tissue and biopsy instruments within the patient's body during a procedure. Such imaging facilitates accurate and controllable removal or sampling of the suspicious tissue so as to minimize trauma to surrounding healthy tissue.

For example, during a breast biopsy procedure, the biopsy device is often imaged with USI while the device is being inserted into the patient's breast and activated to remove a sample of suspicious breast tissue. As USI is often used to image tissue during follow-up treatment, it may be desirable to have a marker, similar to the radiographic markers discussed above, which can be placed in a patient's body at the site of a surgical procedure and which are visible using USI. Such a marker enables a follow-up procedure to be performed without the need for traditional radiographic mammography imaging which, as discussed above, can be subject to inaccuracies as a result of shifting of the location wire as well as being tedious and uncomfortable for the patient.

SUMMARY OF THE INVENTION

The invention is directed generally to devices and methods of marking a biopsy site, so that the location of the biopsy cavity is readily visible by ultrasonic imaging, as well as by conventional imaging methods, such as x-rays. The biopsy site marker of the invention is a persistent marker which may be identified and located by ultrasound visualization.

The biopsy site markers of the invention have a body conformation to enhance acoustical reflective signature or signal. The body conformation may include boundaries of high contrast of acoustic impedance to enhance ultrasound reflection. The markers are readily detected by USI and present a substantial acoustic signature from a marker with small physical dimensions or size. Because of the high acoustic reflectivity of the markers of the invention, the marker size may be reduced to dimensions determined by the physical limits of the imaging system itself, e.g., the ultrasound (US) beam width, without requiring a larger or excessive marker size to reflect sufficient US energy to be noticeable.

In one embodiment, the biopsy site markers of the invention have a characteristic body shape which is recognizably artificial during medical imaging, so as to be readily distinguishable from biological features within the marked tissue. In particular, the markers are readily distinguishable in the various imaging procedures from diagnostically important tissue features, such as lines of calcifications which frequently are signs for a developing malignancy. The marker body shape may have one or more distinct features which may be visualized in different marker orientations. The shape may correspond to a generally known symbol, so a to enhance recognition.

In another embodiment, the markers of the invention have a body conformation to enhance the acoustic signature or signal, so that the body has high acoustic reflectivity when situated in tissue. The acoustic reflective signature of the markers depends on a number of factors. The marker may comprise a composition which presents at least one boundary of high contrast in acoustic impedance to incident US energy, effectively reflecting the US energy to be received by the imaging system. Acoustic impedance (AI) of a material is equal to the product of the characteristic density ($\rho$) of the material and the acoustic velocity (c) in the material, (i.e., AI=$\rho \times c$). As an incident US beam encounters a boundary with a large change in acoustic impedance (e.g., at the marker surface or internal to the marker), much of the US energy is effectively reflected.

Different types of tissue have a wide range of acoustical impedance, for example lung tissue with high air content having low acoustical impedance as compared to bone tissue having high mineral content. However, for uses such as biopsy site marking in typical mammalian soft tissue of high aqueous content, the typical range of tissue acoustical impedance is intermediate these extremes. The composition and body conformation of the markers of the invention may be selected so as to provide boundaries of high contrast of acoustic impedance with respect to the particular tissue site of use.

In an embodiment of the invention, the marker may have a composition in which a base or matrix substance of the marker body (e.g., stainless steel) has an acoustic impedance substantially higher than the tissue at the marked body site. For example, typical bio-compatible metal materials, such as stainless steel, titanium, platinum and the like, generally have acoustic impedance values in the range of 15 to more than 30 times that of typical soft tissue of high aqueous or fatty content. The high acoustic impedance of the marker body base material relative to the surrounding tissue presents a reflective interface to an incident US beam.

A suitable marker body composition with acoustic impedance substantially higher than the tissue at the marked body site is 316L stainless steel. Other alternative compositions, such as compositions of bio-compatible metals, ceramics, metal oxides or polymers, or composites or mixtures of these materials, may be suitable. The marker body may also be radio-opaque.

In another embodiment of the invention, the marker may have a composition in which marker body includes one or more (preferably a large plurality) of internal bounded spaces, such as voids, pores, discontinuities, inclusions, bubbles and the like. These internal spaces preferably contain or entrain air or other gases.

Air has an extremely low acoustic impedance relative to the marker body base or matrix substance. This is true even for matrix materials which themselves have acoustic impedance close to that of the surrounding tissue (e.g., some bio-compatible polymers). The marker body presents internal boundaries of high contrast in acoustic impedance, i.e., at the boundary between the matrix and each internal air-filled space. The marker body thus presents plurality of reflective interfaces to an incident US beam.

Alternatively or in combination with to the materials of high acoustic impedance described above, a marker body with internal voids or air spaces may, if desired, comprise a matrix or base composition which has an acoustic impedance close to that of the tissue at the marked body site, since the air or other gas within the internal spaces provides a dramatic contrast to the matrix material. Suitable bio-compatible materials include polyethylene, polytetrafluoroethylene, PEBAX (made by Autochem Corp.), and the like.

The body matrix material can have a hydrophobic composition or be treated to be hydrophobic. The surface area bounding internal open-cell pores should be hydrophobic so as to resist the displacement of air or other gases in the pores by aqueous fluid from the surrounding tissue, particularly in the case of relatively large pore or space size.

In some embodiments of the invention, the markers can include surface characteristics which enhance the acoustic signature and improve visibility under US imaging, as opposed to a smooth, rounded body surface. In order to provide enhanced ultrasound imaging visibility from all directions of US impingement, the biopsy marker can have a plurality of reflective external surfaces. By making the surface of an object lobulate, multifaceted or otherwise irregular, more reflective surfaces are created, and a brighter acoustic signature is achieved.

For example, a smooth solid sphere provides at least some reflective surface oriented in each direction, but the reflection is achieved over a small portion to the area of the sphere, thus producing an unremarkable acoustic signature. In contrast, an object of the same composition and average diameter as the sphere, but with a highly irregular surface texture, a much brighter acoustic signature or signal is achieved. Thus, the by providing more reflective surfaces of differing or random orientation, the markers appears brighter in US imaging.

The signal-enhancing body conformation may include non-smooth surface texture, such as a porous, frosted, matte, pitted, peened, or scratched surface texture, and the like. The body conformation may also include a multi-element surface contour, such as a faceted, multi-planar, lobulate, coiled, grooved, folded, or inlet surface contour, and the like. Such external body conformations may be used in combination with one another and in combination with the internal discontinuities or air spaces described above.

The body length, diameter or other characteristic scale dimensions of some embodiments of the biopsy marker of the invention may be of a range of sizes. The optimum dimensions of the body will depend upon the specific selected factors which influence acoustic signature as described herein, such as material impedance, surface contours, surface texture, and internal conformation. In addition, the optimum size may depend upon such factors as the type of ultrasound imaging/visualization system used, its imaging resolution, the operating ultrasound frequency, and the biophysical nature of the tissue of interest.

The body dimensions may be selected so as to be large enough to provide a distinct, recognizable marker image within the tissue biopsy site, when visualized under the particular imaging system and operating conditions of use. The body dimensions may also be selected to be small enough to avoid masking or obscuring diagnostically important tissue features. Thus different marker dimensions may be selected to suit particular biopsy site tissue types, and to suit particular known and future medical imaging equipment.

In terms of over-all size, it is desirable that the marker have at least one dimension which is about as large as or greater than the beam width of the USI system with which it is to be visualized. Typically, for current USI systems, the marker will have at least one dimension of about 1 mm or greater, and preferably of at least about 1.5 mm.

In addition, for convenience in applying the marker to the tissue site, the specific marker dimensions and shape may be selected so as to accommodate the dimensions of a particular known or novel biopsy needle device or sampling apparatus, while still achieving a distinct and recognizable marker image under medical imaging as placed at the tissue site. By selecting a marker size and shape to fit within the internal diameter of a biopsy needle or sampling device, the marker may be implanted or applied to the biopsy cavity during the course of the biopsy procedure, following sample recovery but prior to removal of the biopsy device. For example, the marker of the invention may have a size and shape selected to permit application of the marker through the hollow interior space of a vacuum assisted large core biopsy device, such as is commercially available from Johnson and Johnson, Ethicon Endosurgery Division. The small physical size of the markers of the invention relative to their acoustic reflectivity permits fitting the markers to a wide variety of biopsy devices.

In terms of the size of features, including external or internal pores, texture features, facets and the like, it is preferable that these features have a characteristic dimension approximately equal to or exceeding the wavelength of the US beam of the imaging system. For example, with current imaging systems, for a marker with internal air-filled pores, the pore size is typically from about 1 micrometer to 100 micrometers and preferably from about 5 micrometers to 40 micrometers, to provide high reflectivity of the incident US energy.

Optionally, some embodiments of the biopsy site marker of the invention may have elements which assist in accurately fixing the marker to the biopsy site so as to resist migration from the biopsy cavity. Such migration can occur when a placement instrument is withdrawn, and when the marked tissue is subsequently moved or manipulated, as for example when a breast is decompressed and removed from the mammography apparatus. In one embodiment, one or more tissue engaging structures or haptic elements are mounted or affixed to the main marker body, so as to resist movement or migration of the marker from the biopsy site in which it has been implanted during use.

In another embodiment, the biopsy site marker may comprise a pellet-shaped element which encapsulates the high impedance marker body, and assists in resisting migration. The encapsulating pellet may be of a composition, such as gelatin, which is absorbed or dissipated over time, leaving the persistent marker body at the tissue site. In yet another embodiment, the marker body (and/or the optional encapsulating element) may include an adhesive component to cause the marker body (or encapsulating element) to adhere to adjacent tissue within the biopsy site.

A method of the invention for marking a tissue site of interest can include implanting one or more of the markers of the invention, such as one of the exemplary marker embodiments described herein, in or adjacent to a tissue site of interest, e.g., within a biopsy cavity. The marker may then be visualized in situ, such as for purposes of subsequent medical and surgical procedures. The visualization may be by various known medical imaging systems and methods, and in particular may be visualized by known USI systems.

Biopsy markers of the invention can be deposited in accordance with the various methods and techniques utilized in the state of the art. One technique of applying the biopsy markers of the invention is to place or deposit them in a biopsy cavity that is created with a vacuum assisted large core biopsy device. An applicator particularly suitable for insertion of the biopsy site markers of the invention is described below. However, it should be understood that the biopsy markers of the invention can be used without the exemplary applicator device described herein. The biopsy marker applicator disclosed in co-pending application Ser. No. 09/343,975 filed Jun. 30, 1999, may be used to apply the markers of the current invention to a biopsy site. The dimensional size of the applicator device (particularly the inside diameter) may be adjusted to correspond to a selected diameter or characteristic dimension of the biopsy site marker embodiment of the present invention.

These and other advantages of the invention will become more apparent from the following description when taken in conjunction with the accompanying drawings.

DETAILED DESCRIPTION OF THE INVENTION

The following detailed description, and the accompanying drawings to which it refers are provided for purposes of exemplifying and illustrating representative examples and embodiments of the invention only, and are not intended to limit the scope of the invention in any way, and do not exhaustively illustrate and describe all possible embodiments and configurations in which one or more features of the present invention may take physical form.

All patents and patent applications cited in this specification are herein incorporated by reference as if each individual patent or patent application were specifically and individually indicated to be incorporated by reference.

Figure 1:
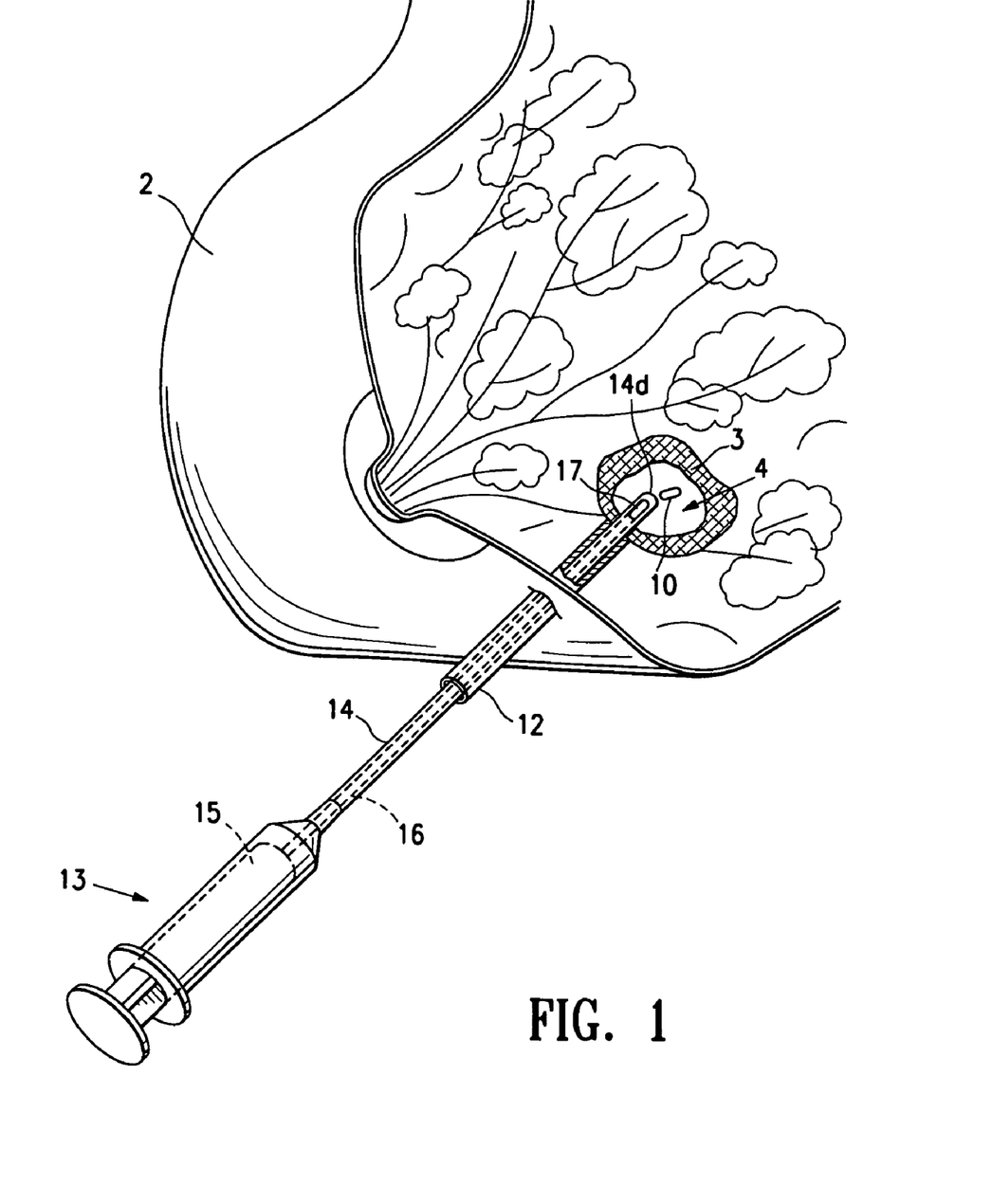
FIG. 1 is a perspective view of a human breast partially cut away having a lesion from which a biopsy specimen has been removed, and showing a marker applicator syringe and introduction cannula operatively positioned for introduction of a biopsy site marker embodying features of the present invention into the cavity created by removal of the biopsy specimen.

FIG. 1 shows the use and insertion into a biopsy site of any one of the biopsy site marker embodiments of the invention described herein. FIG. 1 is a perspective view of a human breast 2 having a lesion 3 from which a biopsy specimen has been removed, thereby forming a biopsy cavity 4 within the lesion 3, into which a biopsy site marker 10 of the of the present invention is implanted. The figure shows an outer cannula 12 with the distal end thereof operatively positioned within the biopsy site 4. The outer cannula 12 has been inserted percutaneously into the lesion 3 and a biopsy needle (not shown) has been passed through the outer cannula 12 and used to remove a biopsy specimen from the center of the lesion.

Syringe-like marker application device 13 includes a marker introduction tube or inner cannula 14. After removal of the biopsy needle (not shown), the marker introduction cannula 14 has been passed through the outer cannula 12 such that inner cannula distal end 14d is located within the biopsy cavity 4, the marker 10 being housed within cannula 14. Piston 15 of marker applicator 13 has an extension 16 which passes through the interior of inner cannula 14. Upon depressing piston 15, extenuation 16 pushes marker 10 outward through an opening 17 in the tip 14d of inner cannula 14 into the cavity 4.

The outer cannula 12 may be an outer tube element of a conventional vacuum assisted large core biopsy device, which has been left in place to assist in site marker application following biopsy sample recovery. One example of a applicator syringe device 13 is described in further detail below with respect to FIG. 5.

FIGS. 2A, 2B, 2C, 2D and 2E show exemplary internal conformations and shapes of the sintered or porous site marker embodiments of the invention 20a-20e respectively.

Figure 2A:
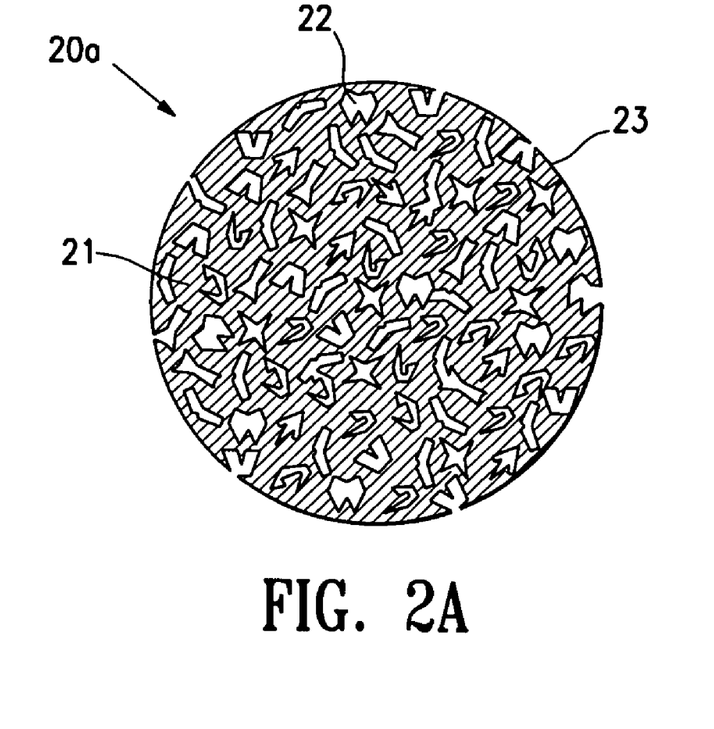
FIGS. 2A-2E show exemplary conformations and shapes of sintered or porous metal site marker embodiments of the invention, FIG. 2A showing a sintered body having irregular pores, FIG. 2B showing a bubble-filled marker body, FIG. 2C showing a cylindrical-shaped marker, FIG. 2D showing a cruciform-shaped marker and FIG. 2E showing a polyhedral shaped marker.
Figure 2B:
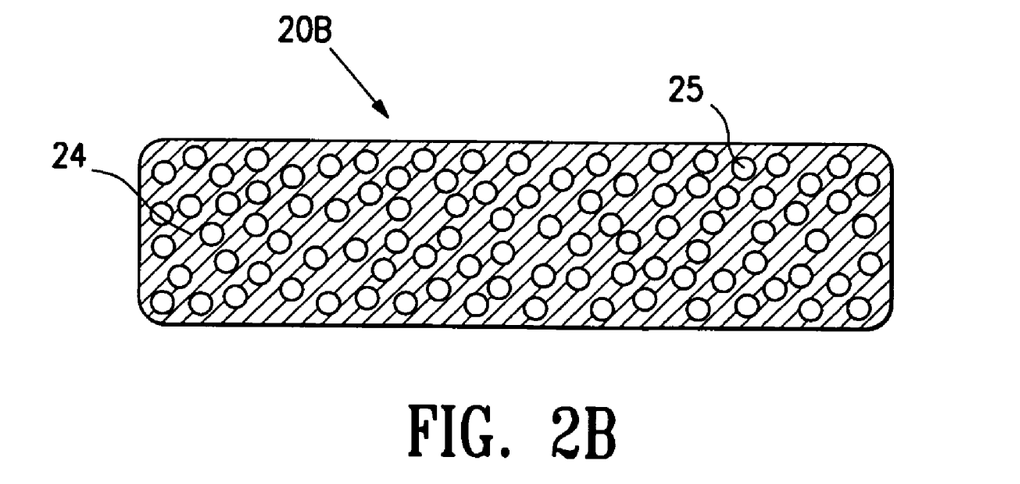

FIGS. 2A and 2B show schematic cross sections of a alternative porous or sintered marker body embodiments. FIG. 2A is a cross section of a sintered site marker embodiment 20a. The matrix or base material 21 encloses a plurality of irregular shaped pores 22 distributed within the body 20a, preferably throughout the body volume. The term "sintered" will be used to describe the porous body conformation, it being noted that conventional methods of production other than sintering may be employed to produce a material containing internal voids, pores, discontinuities, inclusions, bubbles and the like.

The pores 22 may be open celled, in which the pores 22 generally intersect or communicate with one another and the marker body exterior, which may give the body surface 23 a pitted texture on the scale of the pore size. Alternatively, the pores may be closed celled, in which the pores 22 generally do not intersect one another or the exterior. In the event that the pores 22 communicate with the marker exterior 23, the matrix material 21 is preferably hydrophobic (or treated to have hydrophobic surfaces) to resist displacement of air entrained in pores 22.

The base or matrix composition 21 has may be of high acoustic impedance relative to the surrounding tissue (not shown). Sintered metal material may be shaped and sintered from commercially available metallic powders comprising a metal or mixtures of metals, using conventional sintering and forming techniques to produce body of selected shaped, and selected pore size and surface texture, so as to enhance acoustic reflectivity. The porosity of the sintered metal provides an irregular surface texture as well as internal voids. A suitable bio-compatible material is sintered 316L stainless steel, and suitable sintered stainless steel stock is commercially available in various forms, for example from the Mott Corporation. The sintered stock may be economically cut and shaped by conventional methods. Sintered stainless steel stock is commercially available with controlled pore size, selectable over a range of pore sizes. The pores 22 of the sintered body 20a may vary over a range of pore sizes, and is typically from about 1 micrometer to 100 micrometers and preferably from about 5 micrometers to 40 micrometers.

In addition to sintered metal, alternative bio-compatible, impedance materials may be included or substituted, such as ceramics, metal oxides, polymers or composites/mixtures of these materials, which may be configured to have a generally distributed internal porosity and porous surface texture. Thus, the marker body 20a may comprise a matrix or base composition 21 which has an acoustic impedance close to that of the tissue at the marked body site, since the air or other gas within the pores or internal spaces 22 provides a dramatic contrast to the matrix material 21. Suitable bio-compatible materials include polyethylene, polytetrafluoroethylene, PEBAX (made by Autochem Corp.), and the like. Such porous materials may be formed by conventional methods, such as heat bonding of polymer powders, extrusion and the like.

FIG. 2B is a schematic cross section of an alternative site marker embodiment 20b. The matrix or base material 24 encloses a plurality of inclusions, suspended particles or bubbles 25 distributed within the body 20b, preferably throughout the body volume. The inclusions 25 may be low-density or gas-filled particles, such as foamed-in-place bubbles, micro-beads, expanded beads, and the like, which have an acoustic impedance substantially lower than the matrix material 24. The matrix material 24 may as in the example of FIG. 2A.

Figure 2C:
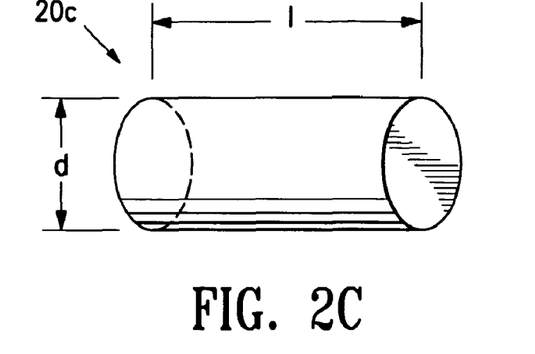
Figure 2D:
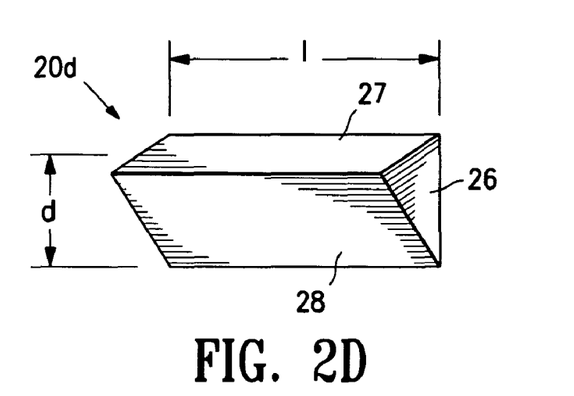

FIGS. 2C and 2D show exemplary shapes of the sintered or porous site marker embodiments of the invention 20c and 20d respectively. FIG. 2C shows schematically a cylindrical sintered marker 20c. The marker 20c comprises a generally cylindrical body having a diameter d and length l. The body may have diameter d of from 0.5 to 5 mm, and preferably about 1.5 mm. The length l may be from about 1 diameters to about 10 diameters, and preferably from about 5 to 7 diameters. This biopsy site marker produces a distinct, recognizable, marker image of artificial appearance when implanted at a depth of about 2 to 4 cm in human breast tissue, and visualized by a commercially available Accuson 128 US imaging system with an L7 transducer.

FIG. 2D illustrates a marker body 20d having a polyhedral form of multiple intersecting flat surfaces 26, 27 and 28.

Figure 2E:
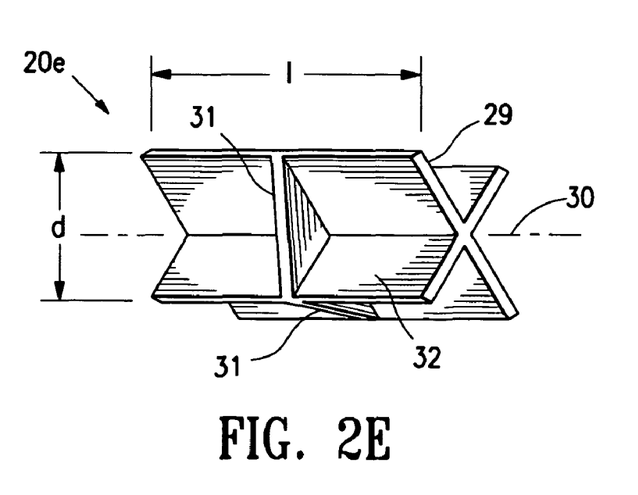

FIG. 2E shows a cruciform shaped marker 20e having cruciform cross-section having four longitudinal fin-like portions 29, which may be aligned at right angles to one another and joined at the longitudinal central axis 30 providing a selectable number of side facets (e.g., hexagonal cross-section). Optionally, medial web portions 31 may span laterally and join between adjacent fins 29, the webs 31 preferably being aligned perpendicularly to the fins 29. In the example shown, there are four such web portions 31 positioned at about mid-length of the body 20e, so that each fin 29 is joined by a pair of webs 31, one on each side, to each adjacent fin. Thus, the planes of the intersecting fins and webs form a pattern of eight mutually-perpendicular "corner reflectors" 32. The length l and characteristic cross-section dimension c may be as described with respect to the embodiments of FIGS. 2C and 2D.

Figure 3:
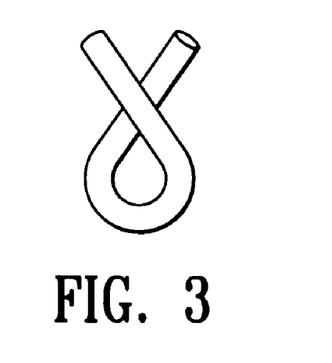
FIG. 3 shows a marker having the shape of a Greek letter.

FIG. 3 illustrates yet another alternative where the marker body is shaped to have the form, under ultrasound or radiological visualization, preferably both, of a familiar symbol or letter, to by easily recognizable as an artificial shape which is the lower-case Greek letter Gamma (γ), which when visualized in a biopsy site bears a resemblance to a familiar breast-cancer-awareness symbol.

Figure 4:
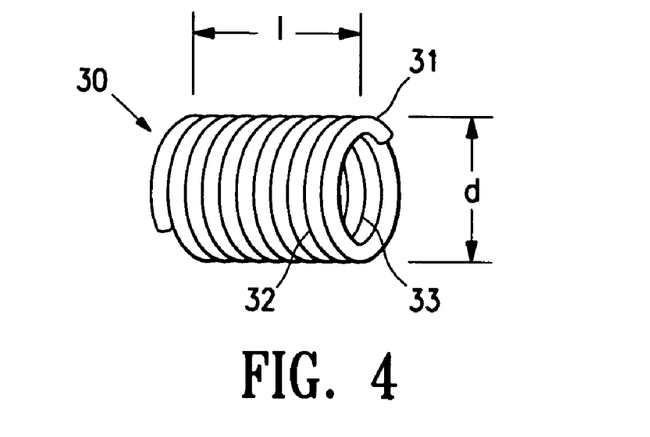
FIG. 4 shows an example of the alternative coil-shaped embodiment of the marker of the invention.

FIG. 4 shows schematically an alternative coil marker 30 of the invention. The marker 30 comprises a generally helical coil-like body formed from one or more lengths of fine wire and/or fiber 31. The coil 30 has a generally cylindrical overall form. As with the other biopsy site marker embodiments of the invention, the optimum dimensions of the coil shaped marker embodiment will depend on such factors as the type of visualization system used, its imaging resolution, and the physical nature of the biopsy tissue region. The coil length l and diameter d may be of a range of sizes, selected so as to be large enough to provide a distinct, recognizable ultrasound marker image within the tissue biopsy site, and small enough to avoid masking or obscuring diagnostically important tissue features. For example, the coil diameter d may be from 0.5 to 5 mm, and preferably about 1.5 mm. The coil length l is typically from about 1 coil diameters to about 10 coil diameters, and preferably from about 5 to 7 coil diameters.

The helical turns of the coil provide a body surface contour including a outer helical groove 32 and inner helical groove 33 on the coil surfaces (more than one such groove for a multiple helix). The grooved coil body surface includes a plurality of lobes and crevices on the exterior of the coil which enhance acoustic reflectivity. In addition the similarly lobed internal surfaces of the coil provide additional reflectivity. Optionally, the coil may be given a "frosted" or textured surface, such as by particle blasting in the manner of the spheroid marker described above. A uniform coil embodiment has a shape which is markedly artificial in appearance under conventional visualization methods, and is not easily confused tissue features of biological origin.

The coil may comprise a fine wire 31 of a material of high acoustic impedance relative to the tissue of the site, and may optionally be radio-opaque. Suitable materials are biologically compatible metals, such as stainless steel, titanium, platinum, palladium, alloys thereof and the like. The coil may alternatively comprise a composite of different materials, such as a composite of metal and polymeric materials. The coil may be wound about a central core of the same or different composition. Coil stock of suitable material, helical form and diameter is available commercially, and may be cut to a selected length by conventional means. A suitable material is 316 L stainless steel surgical embolization coil currently used in arterial embolism repair procedures, e.g., Cook 4 mm diameter embolization coil MWCE-25-2.5-4 of 316L stainless steel and Dacron. Other suitable embolization coil stock is available in a range of coil diameters. This biopsy site marker produces a distinct, recognizable marker image as implanted at a depth of about 2 to 4 cm in human breast tissue, when visualized by a commercially available Accuson 128 US imaging system with an L7 transducer.

Figure 5:
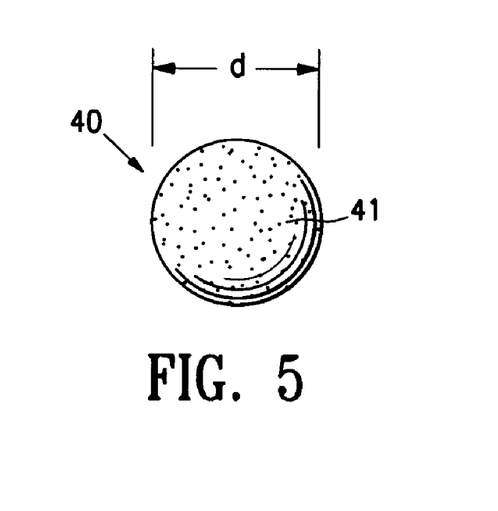
FIG. 5 shows an example of the alternative spheroid embodiment of the marker of the invention.

FIG. 5 shows schematically the alternative spheroid marker 40 of the invention having a generally spherical body 40. Note that the porous or sintered marker embodiments of FIGS. 2A-2D may be spherical also. However, the embodiment of FIG. 5 is a non-porous example, and the biopsy site marker 40 comprises a high acoustic impedance, biologically compatible material, such as 316 L stainless steel and titanium, or radiopaque metals such as platinum, palladium, or the like. Non-spherical shaped bodies may be used, however, metallic spheres of suitable materials are readily commercially available, and have a shape which is markedly artificial in appearance under conventional visualization methods, i.e., not easily confused tissue features of biological origin.

The generally spherical body may have a diameter d selected so as to be large enough to provide a distinct, recognizable ultrasound marker image within the tissue biopsy site, and small enough to avoid obscuring tissue features. As with the other biopsy site marker embodiments of the invention, the optimum size of the sphere will depend on such factors as the type of visualization system used, its imaging resolution, and the physical nature of the biopsy tissue region. For example, the sphere diameter d is typically be from about 1 mm to about 4 mm, and preferably from about 1.5 mm.

The spherical body 40 may include a pitted, matte, peened or frosted surface texture 41, which may be produced by conventional particle blasting or peening techniques. For example, the sphere may be blasted with glass beads of about 100 micrometer diameter to produce a frosted surface. In another example, the sphere may be blasted with aluminum oxide abrasive particles of about 25 micrometer diameter to produce a frosted surface. The frosted surface 41 thus produced provides enhanced acoustic reflectivity in comparison to the untreated, smooth sphere. Other conventional texturing, pitting or faceting methods may alternatively be used to produce a frosted or irregular surface texture.

This biopsy site marker produces a distinct, recognizable marker image of artificial appearance when implanted at a depth of about 2 to 4 cm in human breast tissue, and visualized by a commercially available Accuson 128 US imaging system with an L7 transducer.

Figure 6:
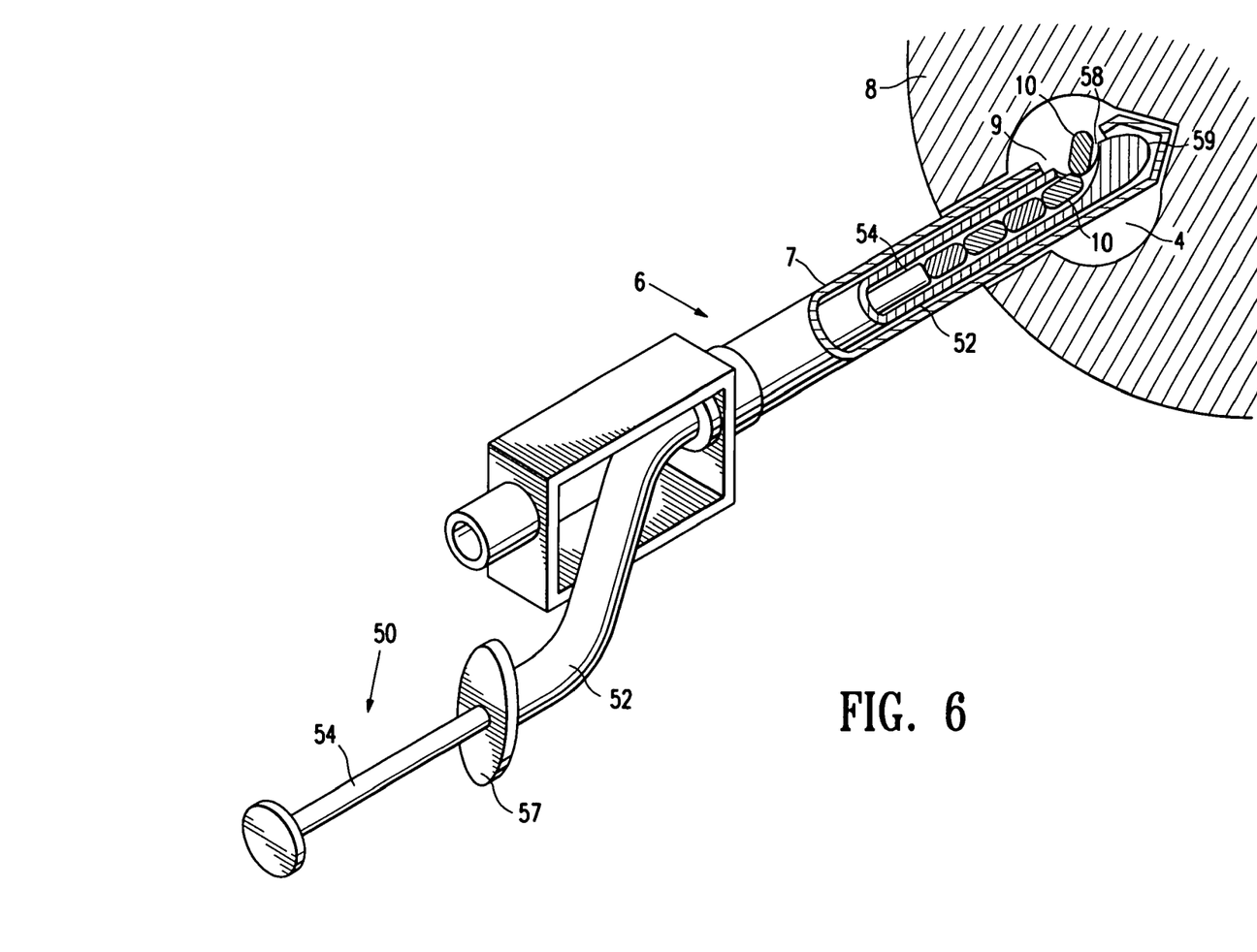
FIG. 6 is a schematic view (scale exaggerated for clarity) of an exemplary biopsy tissue site, in this case a human breast, showing a biopsy cavity of the type obtained by a known type of vacuum assisted large core biopsy sampler device, into which a biopsy marker or markers embodying features of the invention are deposited by a marker applicator device inserted through the outer cannula of the large core biopsy sampler.

FIG. 6 shows schematically in cut-away section an exemplary marker applicator device 50 configured to be operated in association with a conventional vacuum assisted large core biopsy device 6. The dimensional size of the applicator device (particularly the inside diameter) may be adjusted to correspond to the selected diameter or characteristic dimension of the biopsy site marker to be deposited. In this connection it should be understood that the biopsy markers of the invention can be used without this applicator, and can be deposited in accordance with the various methods and techniques utilized in the state of the art.

The applicator 50 comprises an elongated cylindrical body 52 which has an outer diameter selected so that it fits, and may be inserted through, the outer cannula 7 of vacuum assisted large core biopsy device 6. As shown in FIG. 6, the outer cannula 7 is inserted through the biopsy incision into the biopsy cavity 4 previously formed in the patient's tissue site 8, e.g., a human breast in the case of a breast biopsy.

The cylindrical body 52 has an interior cavity and a piston 54 that fits and slides back and forth in the elongated cylindrical body 52. The proximal end of the outer cannula 7 may be provided with rectangularly shaped handle 56 the orientation of which indicates to the operator the orientation of the opening 9 provided in the distal end of the cannula 7. The cylindrical body 52 may have an enlarged finger disk or handle 57 at its outer (exterior to the patient) end which permits a user (not shown) to operate or move the piston 54 within the cylinder 52 of applicator 50. the orientation of the elongated finger disk 57 indicates the orientation of the opening 58 of body 52 adjacent its other, closed end 59 (internal within biopsy cavity). The opening 58 is configured to form a ramp in the side of the tube 52.

In this connection it should be understood that the selected dimensions of the tube 52 are coordinated with the dimensions of the piston 54 and with the cannula 7 of the vacuum assisted large core biopsy device 6, thus permitting the tube 52 to both fit within cannula 7 and to contain one or more markers of the invention 10 within the inside diameter of cylinder 52. The cylinder or tube 52 and the piston 54 may be made from any appropriate medical grade plastic material, such as high density polyethylene or PEBAX, made by the Autochem Corporation.

In one method of implanting the biopsy markers 10 of the present invention, the tube 52 is loaded with one or more of markers 10. The markers 10 may be any of the embodiments of the invention described above, and is shown schematically as a cylindrical object. Optionally, in addition to the markers 10, pellets composed of various other materials may be inserted along with one of the embodiments of the biopsy markers of the present invention described herein. For example, gelatin pellets of the type disclosed in our above referenced co-pending application Ser. No. 09/343,975 may be inserted in conjunction with the biopsy markers 10 of the present invention.

With the markers 10 in the tube 52 and the tube 52 and cannula 7 inserted into the biopsy site 4, the opening 58 in the cylinder 52 is moved into alignment with the opening or port 9 of the in the internal end of cannula 7 of biopsy sampler 6. The piston 54 is pressed inward by the operator so that the marker or markers 10 are expelled from the tube 52 through the ramp shaped opening 58 as the piston 54 is pushed into the cylinder or tube 52. The markers 10 are thereby extruded through opening 59 and port 9 into the biopsy cavity 4. The applicator 50 and biopsy device 6 are subsequently withdrawn.

Figure 7:
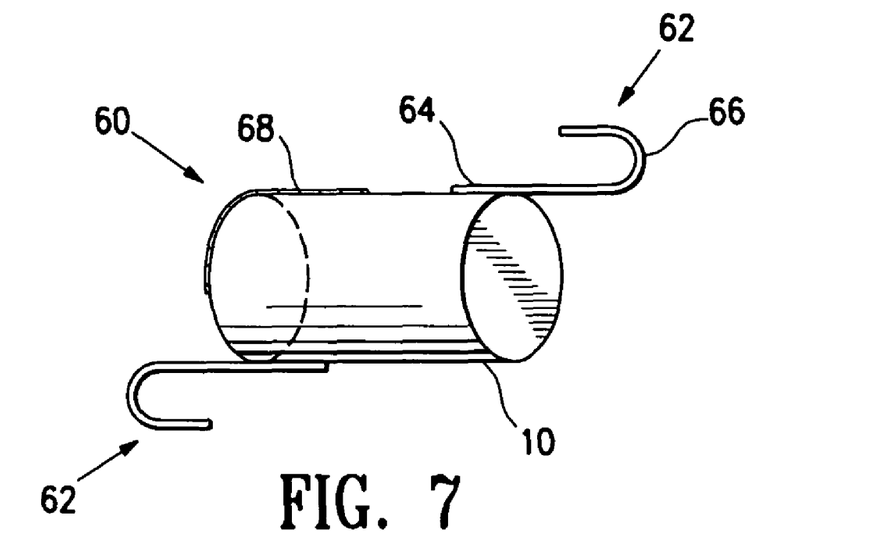
FIG. 7 shows schematically an embodiment of the invention including one or more haptic elements and/or an adhesive component, for resisting migration of the marker within the tissue.

FIG. 7 shows schematically an alternative marker 60 of the invention including one or more optional tissue-engaging or haptic elements 62 for resisting migration of the marker from the biopsy site. An exemplary cylindrical marker body 10 is shown, although each embodiment of the biopsy site marker of the invention described above may optionally comprises one or more such tissue engaging structures. The haptic elements 62 may comprise an wire-like material fixed to the marker body 10 at the proximal haptic end 64 and extending outward from the marker body 10. The haptic 62 may be looped back at its hook-like terminal end 66.

The haptic 62 assists in resisting migration of the marker from the biopsy cavity, during initial placement, i.e., it engages the adjacent tissue to resist being sucked back towards the applicator when the applicator is withdrawn. The haptic also resists migration during later movement, flexure or manipulation of the tissue surrounding the biopsy site, such as when a patient's breast is decompressed upon removal from a mammography device. Optionally, the marker body 10 may include an adhesive component 68 coated onto its surface to cause the marker body to adhere to adjacent tissue within the biopsy site.

Figure 8:
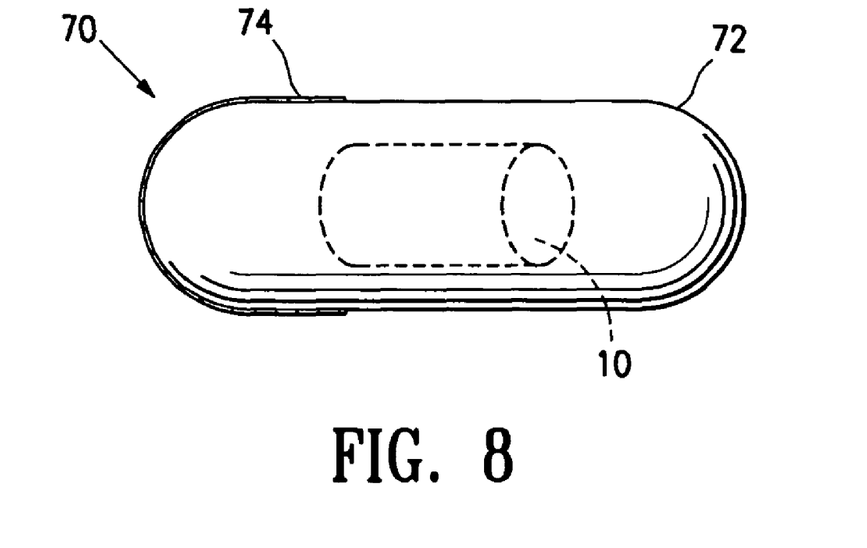
FIG. 8 shows schematically an embodiment of the invention including an encapsulating element and optional adhesive component, for resisting migration of the marker within the tissue.

FIG. 8 shows schematically the alternative marker 70 of the invention including an encapsulating element 72 and optional adhesive layer or component 74, for resisting migration of the marker within the tissue. An exemplary cylindrical marker body 10 is shown, although each of the biopsy site marker of the invention described above may optionally comprise a pellet-shaped encapsulating element.

The pellet-shaped encapsulating element 72 is disposed surrounding the marker body 10 and may fully or partially enclose the marker body. The encapsulating element 72 may be of lower impedance than the metallic marker body 10. Suitable materials are gelatin or reconstituted collagen material, polymers, or mixtures or composites thereof. An optional adhesive component 74 is shown coating the external surface of the encapsulating element, but may be included within the composition the encapsulating element 72.

Figures 9A, 9B, 9C:
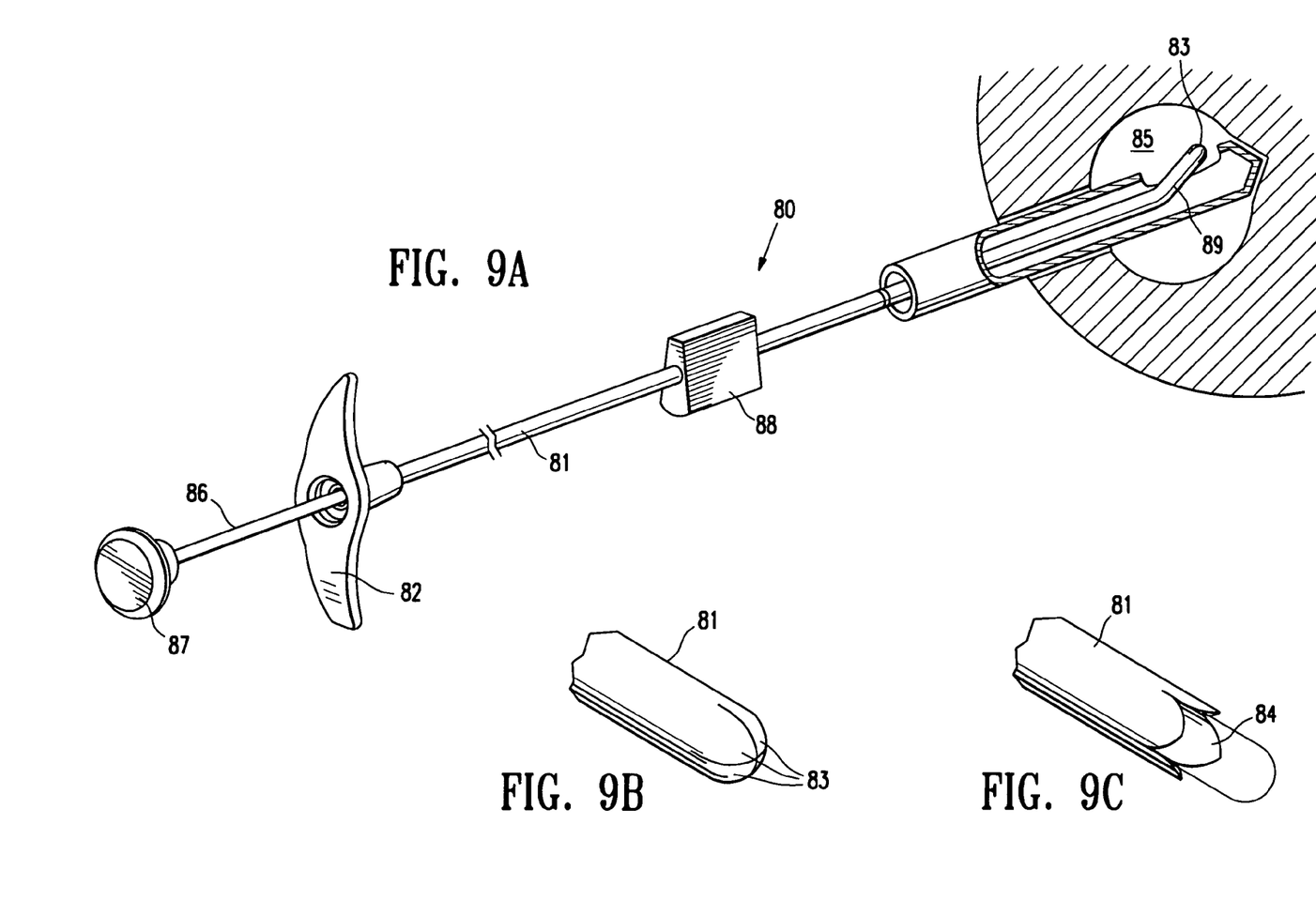
FIG. 9A is a schematic view of a biopsy sampler device at a tissue site with an alternative marker delivery system.
FIG. 9B is a perspective view of the petalled distal end of the delivery device shown in FIG. 9A.
FIG. 9C is a perspective view of the distal end of the delivery device shown in FIG. 9A with a marker exiting the petalled distal end.

FIG. 9A illustrates an alternative device 80 for delivering markers to a biopsy site which includes an elongated tube 81, a handle 82 on the tubes proximal end and a closed distal end having a plurality of leafs or petals 83 as shown in more detail in FIG. 9B. As shown in FIG. 9C, the petals 83 open up to allow a marker 84 to be discharged into the biopsy site 85 as shown in FIG. 9C. The device 80 has an elongated plunger or piston 86 slidably disposed within the tube 81 for pushing one or more markers 84 through the petalled distal end by pressing on the knob 87 on the proximal end of the shaft 86. The orientation of the body 88 on the elongated tube 81 gives the operator an indication of the orientation of the shaped distal end 89.

Figure 10:
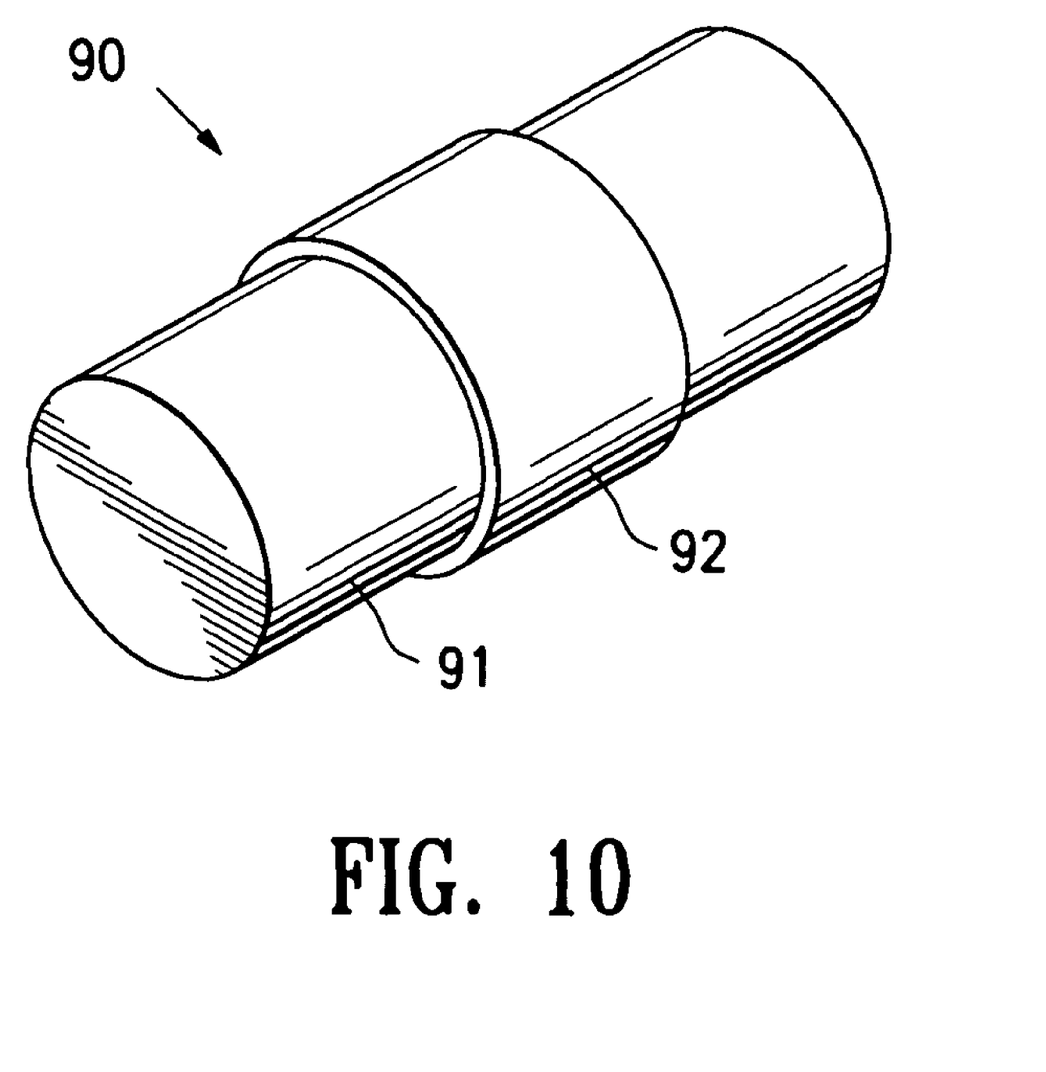
FIG. 10 is a perspective view of an alternative marker having a gel body with a radiopaque collar disposed about the gel body.

FIG. 10 illustrates an alternative marker 90 which has an elongated cylindrically shaped body of gel 91 surrounded with a metallic band 92 which is preferably formed of radiopaque material. The band 92 may completely or only partially surround the body of gel 91.

In any of the above-described embodiments of the invention, the marker body (and/or the optional encapsulating element) may include an adhesive component to cause the marker body (or encapsulating element) to adhere to adjacent tissue within the biopsy site. The adhesive component may comprise a biocompatible adhesive, such as a polyurethane, polyacrylic compound, polyhydroxymethacrylate, fibrin glue (e.g., Tisseal™), collagen adhesive, or mixtures thereof.

While particular forms of the invention have been illustrated and described, it will be apparent that various modifications can be made without departing from the spirit and scope of the invention. Accordingly, it is not intended that the invention be limited to the specific embodiments illustrated. It is therefore intended that this invention to be defined by the scope of the appended claims as broadly as the prior art will permit, and in view of the specification if need be.

What is claimed is:

1. A method of marking a preselected intracorporeal tissue site for a subsequent medical procedure, comprising:
   a. providing a delivery cannula having an inner lumen and at least one marker body slidably disposed within the inner lumen of a delivery cannula, the marker body being formed at least in part of sintered metallic material, is recognized as artificial when remotely imaged by ultrasound and is persistent at the intracorporeal site;
   b. inserting the delivery cannula into the patient and advancing the tube therein until the distal end thereof is disposed at the preselected intracorporeal site; and
   c. discharging the at least one marker at the preselected intracorporeal site so that the at least one marker body is detectable when subject to ultrasound imaging.

2. The method of claim 1 wherein the delivery cannula has a plunger disposed within the inner lumen thereof proximal to the at least one marker body and the at least one marker body is discharged from the delivery tube by distally advancing the plunger within the inner lumen.

3. The method of claim 1 wherein the at least one marker body has boundaries which provide a high contrast in acoustical impedance when placed in tissue of the preselected site, so as to efficiently reflect ultrasound during ultrasound imaging.

4. The method of claim 1 wherein the delivery tube has a ramp which extends to a discharge opening in the distal portion of the delivery cannula and the distal movement of the plunger will move the at least one marker body up the ramp and out of the discharge opening in the delivery cannula.

5. The method of claim 1 wherein the sintered metallic marker body has a porous structure.

6. The method of claim 5 wherein the sintered porous structure has a pore size of about 1 to about 100 micrometers.

7. The method of claim 5 wherein the porous marker body has a pore size of about 5 to about 40 micrometers.

8. The method of claim 5 wherein the sintered porous metallic material is selected from the group consisting of stainless steel, titanium, platinum, palladium and alloys thereof.

9. The method of claim 5 wherein the sintered porous metallic material is titanium.

10. The method of claim 5 wherein at least one marker body which is formed at least in part of sintered metallic material has a spherical shape.

11. The method of claim 1 wherein the at least one sintered metallic marker body is formed of a plurality of metallic particles.

12. The method of claim 1, wherein the sintered marker body has a length and diameter and the length is at least twice the diameter.

13. The method of claim 1, wherein said sintered marker measures approximately 1.5 mm in diameter and 3 mm in length.

* * * * *